(12) United States Patent
Tadesse et al.

(10) Patent No.: US 11,664,130 B2
(45) Date of Patent: May 30, 2023

(54) PREDICTING INFECTION RISK USING HETEROGENEOUS TEMPORAL GRAPHS

(71) Applicant: International Business Machines Corporation, Armonk, NY (US)

(72) Inventors: Girmaw Abebe Tadesse, Nairobi (KE); Chen Lin, Elmsford, NY (US); Roxana Monge Nunez, Perez Zeledon (CR); Maja Vukovic, New York, NY (US); Komminist Weldemariam, Ottawa (CA)

(73) Assignee: International Business Machines Corporation, Armonk, NY (US)

(*) Notice: Subject to any disclaimer, the term of this patent is extended or adjusted under 35 U.S.C. 154(b) by 154 days.

(21) Appl. No.: 17/009,043

(22) Filed: Sep. 1, 2020

(65) Prior Publication Data
US 2022/0068499 A1 Mar. 3, 2022

(51) Int. Cl.
*G16H 50/80* (2018.01)
*G16H 50/50* (2018.01)
(Continued)

(52) U.S. Cl.
CPC ............. *G16H 50/80* (2018.01); *G06N 20/00* (2019.01); *G06Q 30/0205* (2013.01); *G09B 19/00* (2013.01); *G16H 40/20* (2018.01); *G16H 50/20* (2018.01); *G16H 50/30* (2018.01); *G16H 50/50* (2018.01); *G16H 50/70* (2018.01);
(Continued)

(58) Field of Classification Search
CPC ........ G16H 50/80; G16H 40/20; G16H 50/20; G16H 50/30; G16H 50/50; G16H 50/70; G16H 10/60; G06N 20/00; G06Q 30/0205; G06Q 50/01; G06Q 10/0635; G09B 19/00; H04W 4/12; H04W 4/021; H04W 4/029
See application file for complete search history.

(56) References Cited

U.S. PATENT DOCUMENTS

| 8,560,339 | B2 | 10/2013 | Khan |
| 10,188,048 | B2 | 1/2019 | Nelson |

(Continued)

FOREIGN PATENT DOCUMENTS

| CA | 2421523 C | 3/2017 |
| KR | 101875858 B1 | 7/2018 |

(Continued)

OTHER PUBLICATIONS

Authors et al.: Disclosed Anonymously, "Modeling Disease Incidence and Progression Using Deep Neural Networks", An IP.com Prior Art Database Technical Disclosure, IP.com No. IPCOM000252181D, IP.com Electronic Publication Date: Dec. 20, 2017, 5 pages.

(Continued)

*Primary Examiner* — Eliza A Lam
(74) *Attorney, Agent, or Firm* — David K. Mattheis

(57) ABSTRACT

Predicting infection risk by generating a first temporal graph of a first set of disease progression data, generating a second temporal graph of a second set of disease progression data, combining a first temporal graph node embedding and a second temporal graph node embedding, and generating a predicted infection risk according to the first temporal graph node embedding and the second temporal graph node embedding.

20 Claims, 5 Drawing Sheets

200

(51) Int. Cl.
| | |
|---|---|
| *G16H 50/70* | (2018.01) |
| *G16H 40/20* | (2018.01) |
| *G06Q 30/0204* | (2023.01) |
| *G16H 50/30* | (2018.01) |
| *G06N 20/00* | (2019.01) |
| *H04W 4/12* | (2009.01) |
| *G09B 19/00* | (2006.01) |
| *G16H 50/20* | (2018.01) |
| *H04W 4/021* | (2018.01) |
| *G16H 10/60* | (2018.01) |
| *H04W 4/029* | (2018.01) |

(52) U.S. Cl.
CPC .............. *H04W 4/12* (2013.01); *G16H 10/60* (2018.01); *H04W 4/021* (2013.01); *H04W 4/029* (2018.02)

(56) References Cited

U.S. PATENT DOCUMENTS

| | | | |
|---|---|---|---|
| 10,251,610 | B2 | 4/2019 | Parthasarathy |
| 2015/0012292 | A1 | 1/2015 | Khan |
| 2015/0170296 | A1 | 6/2015 | Kautz |
| 2017/0024531 | A1 | 1/2017 | Malaviya |
| 2019/0180841 | A1* | 6/2019 | Douglas .................. G16H 50/20 |
| 2021/0233658 | A1* | 7/2021 | Van Assel .............. G16H 70/60 |

FOREIGN PATENT DOCUMENTS

| | | | | |
|---|---|---|---|---|
| WO | WO-2010088672 | A1 * | 8/2010 | ......... G06K 9/00147 |
| WO | 2019038271 | A1 | 2/2019 | |

OTHER PUBLICATIONS

Huang et al., "Graph Recurrent Networks with Attributed Random Walks", Research Track Paper, KDD '19, Aug. 4-8, 2019, Anchorage, AK, USA, pp. 732-740.

Mell et al., "The NIST Definition of Cloud Computing", Recommendations of the National Institute of Standards and Technology, Special Publication 800-145, Sep. 2011, 7 pages.

Singer et al.,"Node Embedding overTemporal Graphs",arXiv:1903. 08889v2 [cs.LG] Apr. 2, 2019, 11 pages.

\* cited by examiner

PREDICTING INFECTION RISK USING HETEROGENEOUS TEMPORAL GRAPHS

BACKGROUND

The disclosure relates generally to infection risk prediction. The disclosure relates particularly to infection risk prediction using node embedding over heterogeneous temporal graphs.

Infectious diseases are a leading threat to public health and societal stability. Disease control revolves around health surveillance systems that track the spread of diseases and associated clinical outcomes.

SUMMARY

The following presents a summary to provide a basic understanding of one or more embodiments of the disclosure. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatuses and/or computer program products enable the generation of predicted infection risks.

Aspects of the invention disclose methods, systems and computer readable media associated with predicting infection risk by generating a first temporal graph of a first set of disease progression data, generating a second temporal graph of a second set of disease progression data, combining a first temporal graph node embedding and a second temporal graph node embedding, and generating a predicted infection risk according to the first temporal graph node embedding and the second temporal graph node embedding.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Figure 1:
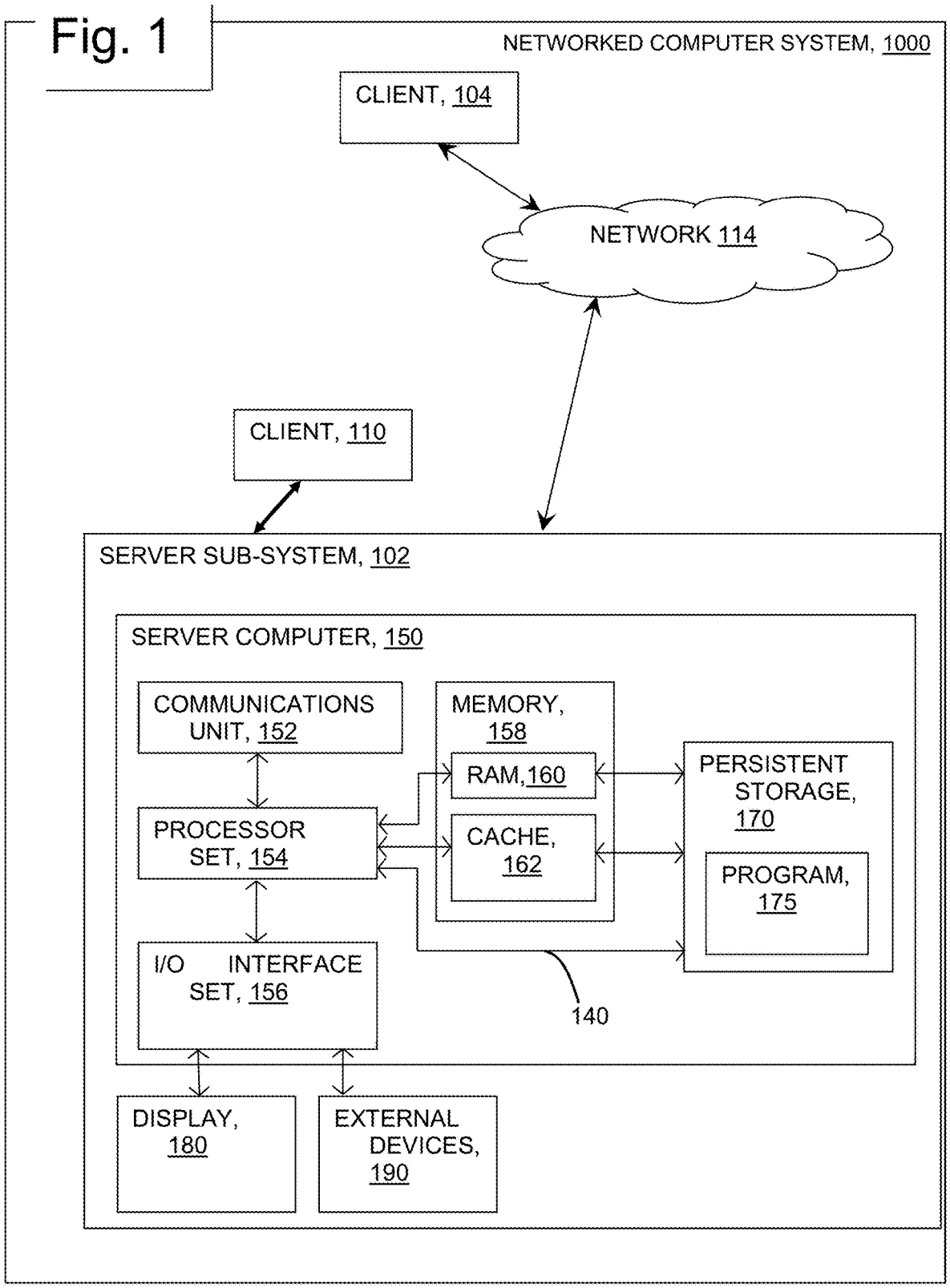
FIG. 1 provides a schematic illustration of a computing environment, according to an embodiment of the invention.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

In an embodiment, one or more components of the system can employ hardware and/or software to solve problems that are highly technical in nature (e.g., generating first and second temporal graphs from first and second sets of disease progression data, combining node embeddings from each of the first and second temporal graphs, generating infection risk predictions according to the combined node embeddings, etc.). These solutions are not abstract and cannot be performed as a set of mental acts by a human due to the processing capabilities needed to facilitate predicting infection risks, for example. Further, some of the processes performed may be performed by a specialized computer for carrying out defined tasks related to predicting infection risks. For example, a specialized computer can be employed to carry out tasks related to infection risk prediction, or the like.

Health surveillance systems structured to assist in the management of infectious diseases tend to include slow and expensive data collection processes. The systems also include time lags relating to the progression of a disease, have low levels of temporal and spatial resolution and tend to be limited in terms of their disease spreading modalities. Disclosed systems and methods provide predictions of infection risks enabling rapid responses to spreading infections, providing behavioral guidance for individuals, and enabling the creation of dynamic geo-fencing safe and hot zones.

Aspects of the invention disclose methods, systems and computer readable media associated with predicting the temporal patterns of disease progression using temporal graph embedding on a social network. Further, learning the disease severity in a location/city and the speed of disease spread due to mobility patterns across different modalities (e.g., flight and/or ground transportation) using attributed random walk on city network. Aspects also disclose detecting a subset of interactions (nodes/group) that are susceptible using subset scanning methods to identify a cluster of interactions that possess peculiar characteristics compared to the average population dynamically creating geo-fencing zones/locations for the predicted risk of infection of a disease based on projected disease spread analysis. The disclosure also includes intervention planning using machine learning algorithms (e.g., reinforcement learning), by (i) optimizing a route for a user or group based on predicted geo-fencing zones, and/or (ii) alerting a user or group of users traveling together regarding nearby geo-fenced hot zones.

Aspects of the invention disclose methods, systems and computer readable media associated with predicting the likelihood of an individual becoming infected using node embedding over heterogeneous temporal graphs; predicting the likelihood that an individual moving from a first location A to a second location B, will become infected; identifying and profiling hot spot locations in a geographic area, where the risk of infection is high due to factors such as weather, crowd-density, etc.; creating dynamic safe/hot geo-fence boundaries according to the identified hot spot locations, and altering the boundaries as the risk of infections and hot spot locations and boundaries change; and generating alerts to individuals or authorities as safe/hot boundaries are approached or crossed.

Aspects of the invention disclose methods, systems and computer readable media associated with predicting infection risk including back tracing individual interactions over time to identify other individuals or groups who have come into contact with an infected individual, or who have visited a particular location/area identified as a hot spot.

Aspects of the invention disclose methods, systems and computer readable media associated with predicting infection risk including computing multi-dimensional risk scores with consideration for the health care system capabilities of an evaluated geographic area, i.e., taking into consideration the impact upon the spread of a disease that the capability of a local health care system has to deal with the spread of a disease, or be overwhelmed by the disease.

As a non-limiting example, the following discussion is provided in terms of human individuals. The disclosed inventions are not limited to the prediction of infection risks among a human population and may further be applied to the prediction of infection risk among any animal population.

In an embodiment, the method generates a set of temporal graphs from a first set of disease progression data. In this embodiment, the disease progression data includes personal data for an individual including social network data relating to the personal contacts of the individual. In an embodiment, the disease progression data also includes one or more of: an individual profile including age, gender, current location, credit-debit card usage (associated with location tracking), the individual's personal health history, current health status and any active symptoms evidenced by physiological signals including body temperature, heart rate, blood oxygen level, respiration rate, etc., as provided by one of more internet of things devices linked to a disease progression data gathering network system, self-reported symptoms from social media postings, social network tagging related to current and previous locations as well as current and previous contacts, thermal imaging data from drones or surveillance systems, location tracking data from smart devices or radio-frequency identification tags, and so on. In an embodiment, the method further considers the prior health conditions, socio-economic status, mobility patterns and interaction frequencies of the respective individuals. In any embodiment, each user "opts in" to the gathering and use of their personal data by the disclosed systems and methods. The disclosed systems and methods implement an end-to-end encryption protocol to protect the personal data from any misuse.

In an embodiment, the method computes a node embedding for an individual based upon personal data—the individual's social network modelling including their personal interactions. The method further computes a node embedding based upon the local environment of the individual—the city model including the disease progression data for the local geographic area of the individual—the number of known and suspected infections, the modes of transportation to and within the area, crowd densities, public events, and personal interactions of the city residents, the current weather and so on.

In this embodiment, the node embedding from the personal model and the geographic model are combined and provided to a trained machine learning model, which provides a prediction of the infection risk for the individual in their current area as well as a prediction of the risk associated with travel to a new area.

In an embodiment, the method applies subset scanning to the machine learning neural network activations to identify anomalous nodes (interactions) associated with the node embeddings. Subset scanning detects the processing of anomalous input data. In this embodiment, the detected subset of anomalous nodes, taken as a group, indicate an increased infection susceptibility.

In an embodiment, the method generates sets of heterogeneous temporal graphs from the provided data corresponding to the available time slices or discernible moments in time extractable from the data. Different data sets yield different levels of temporal resolution for the temporal graphs. In response to generation of the set of temporal graphs, the method generates node embeddings for each node of each of the temporal graphs of the set. In an embodiment, each node represents a different individual. Temporal graphs are generated for the individual's personal network and environmental (city or area) network data.

As an example, for a temporal graph $G=(V,E)$, where V represents graph vertices, and E represents graph edges between vertices, each temporal edge $(u,v)_t$ as an element of E is an edge between vertices u and v at time t. Temporal graph $G_t=(V_t, E_t)$ represents the graph of all vertices and edges up to and including time t. In this embodiment, the method computes the node embedding $f_T(t)$ for each node v at time t. In an embodiment, the method computes the embedding of node v at time t+1 using the recursive representation $$f_{t+1}=\sigma(Af_t(v)+BQ_tR_tv)$$

where σ represents an activation function, v is the one-hot encoding of a node, and A, B, Qt, and Rt are learned during training of the temporal graph to jointly optimize node dynamics using data. Qt constructs the node embedding according to the historical node snapshots and Rt represents a rotation metric used to enforce the alignment of node embedding between consecutive time steps represented by successive temporal graphs using an algorithm that learns features via joint optimization of preserving network structure and network dynamics in temporal networks, for example, using Expectation Maximization.

In an embodiment, the node embedding $g_{ti}$ for node i in the city network can be learned using an attributed random walk. In generating the successive frames of the attributed random walk, the method considers all individual attributes subject to change from one frame to the next, health status for example, in addition to location. The method then randomly determines the attributes of the next frame. In an embodiment, the random selection is biased according to previously predicted probabilities or according to travel modality probabilities. Examples include using a predicted infection rate for an area, predicted local weather conditions and a predicted crowd density, in determining the next health status of an individual. or using the probability of each of walking, taxi use, train and bus use, in determining how large a location change is likely for an individual. The method defines and constructs a bipartite network to enable joint walks within the network attributes and node attributes. Specifically, nodes have some probability of jumping to other node and attribute categories between temporal slices. For each node $i \in V$, the method draws a small sample of sequence $\tau_i$ which takes i as starting node. The method applies a graph recurrent network to learn the embedding for each node. The method applies pooling to fuse node representation of the node in $\tau_i$. In an embodiment, the pooling operation is the mean of different embedding vector representations, obtained from the indices in sequence set $\tau_i$.

After determining the social network node embedding and the city network node embedding, the method multiples the two node embeddings yielding a combined node embedding. In an embodiment, the method provides the combined node embedding as input to a trained machine learning model configured to process temporal sequence input data—such as a Long Short-term memory (LSTM) model. The trained machine learning model captures and extracts temporal dependencies present in the combined embeddings. The output of the trained model provides an infection risk probability associated with an individual, a geographic location or the combination thereof. Taken as measure across a population over time, the output provides an infection rate for the population or area at a given time. For example, the method determines the infection risk for each individual among a population of an area from one week to the next. The method also determines a weekly infection rate as the percent of that population predicted to shift to a status of infected over the course of that week.

In an embodiment, the method considers health care system capabilities of an area in predicting infection rates. Using the combination of predicted infection rate and health care system capabilities, the method predicts whether, and if so when, local health care systems will become overwhelmed dealing with the disease progression, and adjusts the infection rates for the area accordingly—infection rates typically accelerate after local health care systems are overwhelmed. In this embodiment, the method considers health care system data including items such as number of beds, number of health care professionals, health care professional specializations, locally available medical supplies, medications personal protective equipment, specialized medical equipment need for dealing with a disease therapeutically, etc. Such data can be extracted from medical supply chain networks.

In an embodiment, training the machine learning model includes finding a feature vector for each node $v \in V$ at time T that minimizes the loss of the prediction task. In this embodiment, the method considers a categorical cross-entropy loss:

$$L_{task} = -\Sigma_{v \in V} \log Pr(\text{class}(v)|f_{T_v}, g_{T_v})$$

where $\log Pr(\text{class}(v)|f_{T_v}, g_{T_v})$ represents the logistic probability of a node, represented by a feature vector v, being classified as to a set of possible labels. For example, a label could be a person's role in a social network or the probability whether two users in a social network are friends.

In this embodiment, the method optimizes the learning problem by minimizing the loss function:

$$L = \min L_{task} A, B, Q_1, \ldots Q_T, R_1, \ldots, R_T.$$

In an embodiment, due to the sparsity of labels for input data, the method applies Expectation Maximization during model training to learn the parameters including A, B, $Q_t$, and $R_t$. In this embodiment, the method initializes the parameters related to the node dynamics (A, B, $Q_t$, and $R_t$) with random values. The method then computes the predicted infection risk P according to the random parameter values. The method then uses the estimated P to generate new parameter values for A, B, $Q_t$, and $R_t$. The method iterates these steps, estimating parameters, computing P, and revising the parameters until the parameter and calculated infection risk values converge on stable values.

In an embodiment, the output indicates the probability of infection as well as the predicted rate at which an individual can infect others in their social network and the impact their infection has upon the infection rate of their current city. In this embodiment, the output provides an indication of locations having higher or lower infection rates—hot and safe spots respectively. The identification of safe and hot spots from the trained model output enables the generation of mappings of safe and hot zones, as well as the identification of geo-fence boundaries between the safe and hot zones. The output further enables the generation of routing information to enable an individual to transit from a first safe location to a second safe location while minimizing their risk of infection. In this embodiment, the method considers the current location, the desired destination location and the current infection risks associated with locations between the two. The method selects random routings between locations and calculates overall infection risks for the selected routings. In this embodiment, the method identifies the routing having the lowest risk of infection for the individual.

In an embodiment, the method utilizes the output to predict the likelihood of an individual becoming infected when traveling from a first location to a second location. The method considers the respective likelihoods of the origin and destination locations as well as the intervening locations and available modes of transportation between origin and destination locations.

FIG. 1 provides a schematic illustration of exemplary network resources associated with practicing the disclosed inventions. The inventions may be practiced in the processors of any of the disclosed elements which process an instruction stream. As shown in the figure, a networked Client device 110 connects wirelessly to server sub-system 102. Client device 104 connects wirelessly to server sub-system 102 via network 114. Client devices 104 and 110 comprise infection prediction program modules (not shown) together with sufficient computing resource (processor, memory, network communications hardware) to execute the program. In an embodiment, client devices 104, and 110, serve as portions of the infection prediction network computing system, providing individual location and health information, social networking data, and receiving alerts regarding infection predictions and hot zone boundaries relative to an individual's location and current routing.

As shown in FIG. 1, server sub-system 102 comprises a server computer 150. FIG. 1 depicts a block diagram of components of server computer 150 within a networked computer system 1000, in accordance with an embodiment of the present invention. It should be appreciated that FIG. 1 provides only an illustration of one implementation and does not imply any limitations with regard to the environments in which different embodiments can be implemented. Many modifications to the depicted environment can be made.

Server computer 150 can include processor(s) 154, memory 158, persistent storage 170, communications unit 152, input/output (I/O) interface(s) 156 and communications fabric 140. Communications fabric 140 provides communications between cache 162, memory 158, persistent storage 170, communications unit 152, and input/output (I/O) interface(s) 156. Communications fabric 140 can be implemented with any architecture designed for passing data and/or control information between processors (such as microprocessors, communications and network processors, etc.), system memory, peripheral devices, and any other hardware components within a system. For example, communications fabric 140 can be implemented with one or more buses.

Memory 158 and persistent storage 170 are computer readable storage media. In this embodiment, memory 158 includes random access memory (RAM) 160. In general, memory 158 can include any suitable volatile or non-volatile computer readable storage media. Cache 162 is a fast memory that enhances the performance of processor(s) 154 by holding recently accessed data, and data near recently accessed data, from memory 158.

Program instructions and data used to practice embodiments of the present invention, e.g., the infection prediction program 175, are stored in persistent storage 170 for execution and/or access by one or more of the respective processor(s) 154 of server computer 150 via cache 162. In this embodiment, persistent storage 170 includes a magnetic hard disk drive. Alternatively, or in addition to a magnetic hard disk drive, persistent storage 170 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 170 may also be removable. For example, a removable hard drive may be used for persistent storage 170. Other examples include optical and magnetic disks, thumb drives, and smart cards that are inserted into a drive for transfer onto another computer readable storage medium that is also part of persistent storage 170.

Communications unit 152, in these examples, provides for communications with other data processing systems or devices, including resources of client computing devices 104, and 110. In these examples, communications unit 152 includes one or more network interface cards. Communications unit 152 may provide communications through the use of either or both physical and wireless communications links. Software distribution programs, and other programs and data used for implementation of the present invention, may be downloaded to persistent storage 170 of server computer 150 through communications unit 152.

I/O interface(s) 156 allows for input and output of data with other devices that may be connected to server computer 150. For example, I/O interface(s) 156 may provide a connection to external device(s) 190 such as a keyboard, a keypad, a touch screen, a microphone, a digital camera, internet of things devices, and/or some other suitable input device. External device(s) 190 can also include portable computer readable storage media such as, for example, thumb drives, portable optical or magnetic disks, and memory cards. Software and data used to practice embodiments of the present invention, e.g., infection prediction program 175 on server computer 150, can be stored on such portable computer readable storage media and can be loaded onto persistent storage 170 via I/O interface(s) 156. I/O interface(s) 156 also connect to a display 180.

Display 180 provides a mechanism to display data to a user and may be, for example, a computer monitor, or portable user device displaying a predicted level of infection risk, or a predicted safe travel routing. Display 180 can also function as a touch screen, such as a display of a tablet computer. Display 180 provides a way to display method outputs including infection predictions, travel routing, hotspot mapping and infection prediction-based alerts.

Figure 2:
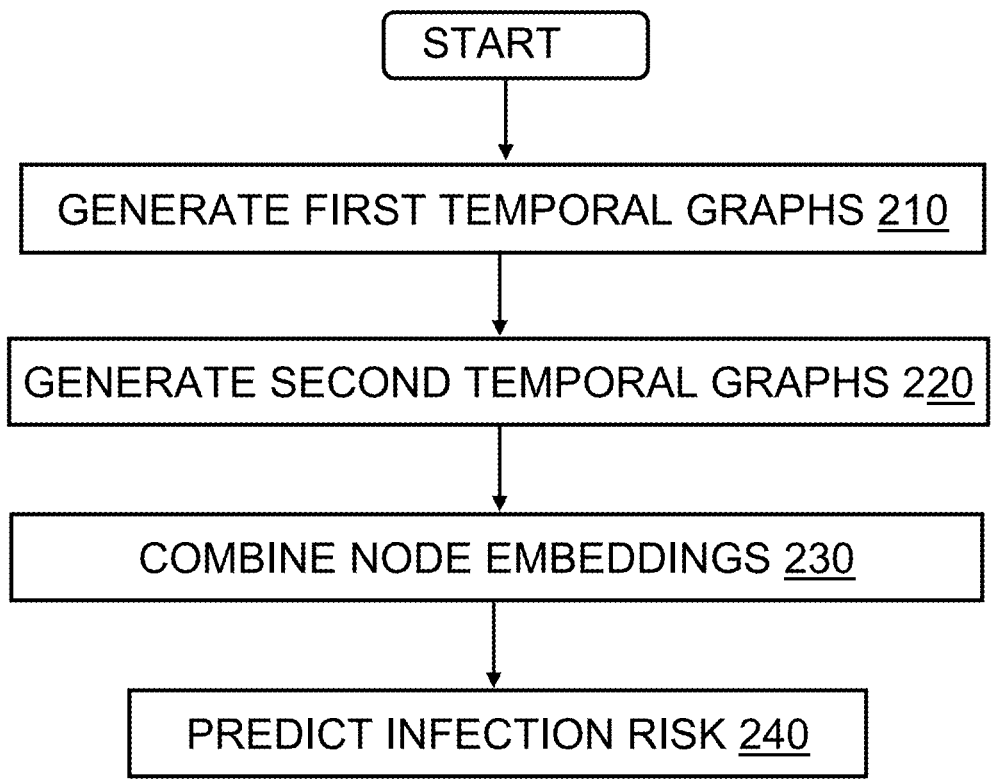
FIG. 2 provides a flowchart depicting an operational sequence, according to an embodiment of the invention.

FIG. 2 provides a flowchart 200, illustrating exemplary activities associated with the practice of the disclosure. After program start, at block 210, infection prediction program 175 generates a first set of temporal graphs. These temporal graphs are generated using data associated with an individual and that individual's interactions within others in a social context—interactions of the individual's choosing with other individuals the first individual knows. In an embodiment, the data includes known contacts, an individual profile including age, gender, current location, credit-debit card usage, location information, electronic health records, and physiological signals—electro-cardiogram, blood oxygen, blood pressure, heart rate, respiration rate, etc., available from connected monitoring devices. In this embodiment, the data also includes crowd sourced data relating to self-reported health symptoms, surveillance data from fixed surveillance cameras as well as moving cameras such as surveillance drones checking individual temperatures, tracking device (RFID) data for individuals or subject animals, social network tag data showing contact between individuals, and other relevant personal network data for an individual. Each temporal graph of the set includes vertices representing individuals and edges representing contacts or interactions between individuals. The set of temporal graphs provide a succession of time slices representing the changes in interactions, and other individual data over time. For example, at a time t1, individuals A and B are in contact, at time t2, A is no longer in contact with B and is alone. At time t3, A is in contact with C, etc. The data further includes a health status—uninfected, suspected infection, or infected—for each of A, B, and C at each time slice. The set of graphs provides data on the travel and interactions of the set of individuals in conjunction with their current health status. In an embodiment, the set of graphs provides data enabling back tracing of an individual's interactions from any point desired, e.g., a point at which the individual tests positive for a disease, enabling determination of those with whom the now infected person has recently been in contact. Such back tracing enables a proactive approach to track the spread of a disease and prevent additional spread by quickly identifying infected individuals with appropriate testing.

At block 220, infection prediction program 175 generates a second set of temporal graphs using area, or city, network information. These temporal graphs provide a succession of time slices showing predicted disease progression across a geographic area and considering individual locations and predicted infection status, transportation modalities—walking, bicycle, scooter, automobile, bus, train, airplane, etc.—to predict possible location changes between successive graphs—pedestrians change locations much more slowly than bus riders, and so on. For air travel, the graphs also consider potential flight origin and destination information, flight duration, number of passengers, likelihood of infected passengers according to origin area infection rates, to predict disease spread from one geographic area to a second area. The method further considers average and predicted local weather conditions, typical crowd density data for the area, event data—holiday timing, sporting events, festivals, etc., in predicting the disease spread across the succession of graphs. Attributed random walks across the area are used in the predictions. The random walks are attributed random walks in the sense that numerous attributes of an individual may change between each data frame of the set of temporal graphs. Exemplary attributes include location, number of close proximity contacts, and infection status. For these attributed random walks, the method considers an individual of a known infection status at a first location, randomly assigns the individual a transport modality and predicts their movement using the modality, as well as their attributed infection status over successive graphs to predict the likely number of interactions of the individual, and the progression of the disease among the collection of individuals overall. For example, uninfected individual A boards a bus at location 1, the bus contains a randomly generated number of passengers, each passenger and the driver having a likelihood of infection determined according to the current infection rate associated with their previous locations and previously determined infection status, and individual A exits the bus at location 2, after a trip of specified duration. A spends 2 hours at a crowded festival with others, each having a predicted infection risk, and returns by bus to location 1 as described above. The method calculates the number of interactions occurring across the area over the succession of temporal graphs, in conjunction with a prediction of infected individuals and with consideration for a known or predicted infection rate between individuals according to contact time. The method predicts an infection level and rate of spread for the area and between areas according to the data and temporal graph methodology.

At block 230, infection prediction program 175 combines a node embedding fi, for an individual at time T, from the first set of personal or social network-based temporal graphs, with the node embedding gi, for an individual at time T within the local area of the individual from the city network temporal graphs. The multiplied combination fi*gi, provides data relating the interactions of the individual according to both their personal network and their local, city-based, environment, with considerations for changes from one area to another area over time. The respective node embeddings provide a mathematical expression of the relationship data embodied in the temporal graph sets. In an embodiment, the node embeddings are determined using graph recurrent neural networks trained to extract social network or geographic area-based node embeddings.

In an embodiment, the combined personal and area node embeddings are passed to a trained machine learning model, such as a trained long short-term memory (LSTM) model. A trained LSTM model receives a series of data frames as input—particularly a succession of time sliced data frames, and outputs a pattern recognized within the input data. In an embodiment, the method trains the LSTM model by providing labeled training data for individual social network temporal graph data node embeddings combined with geographic temporal graph node embeddings. In this embodiment, the social network and geographic area temporal graphs are constructed using labeled individual social network and city attributed random walks.

The method provides input data to the machine learning model and seeks to minimize the loss function as described above. The node weightings of the model are adjusted using back propagation and gradient weighting such that the loss function is minimized over the set of training data. The trained model receives combined node embedding input data and recognizes patterns in the succession of data frames associated with known infection risks for the individual and geographic area. At block 240, the method predicts the infection risk for an individual, a group of individuals, a geographic area, or a combination of these. The method outputs the recognized infection risk for the individual, the area, or both. In an embodiment, the method determines a rate of infection for the area as well by evaluating the rate of individual infection change over time.

In an embodiment, application of the method across a broad geographic area identifies safe zones, hot spots, and the boundary between the two. Gradations of safe and hot are identified according to ongoing changes in the respective rates of infection. In this embodiment, the method calculates safe routes and modalities of transportation for individuals seeking to move from one safe location to another as well as calculating the risk of infection for the travel between safe zones or between safe zones and hot zones.

In an embodiment, the method translates the predicted infection rate for an individual into an alert. In this embodiment, the method communicates the alert to the individual and/or the local and regional authorities. Predictive identification of an area as a hot zone generates an alert for the identified area and enables authorities to act to stem the progression of the disease.

In an embodiment, the alerts are issued to individual mobile device enabling individuals notice of their status. In this embodiment, an individual may receive an alert as they move from a safe zone toward a hot zone, or as they use their device to route travel from a safe zone through a hot zone.

Figure 3:
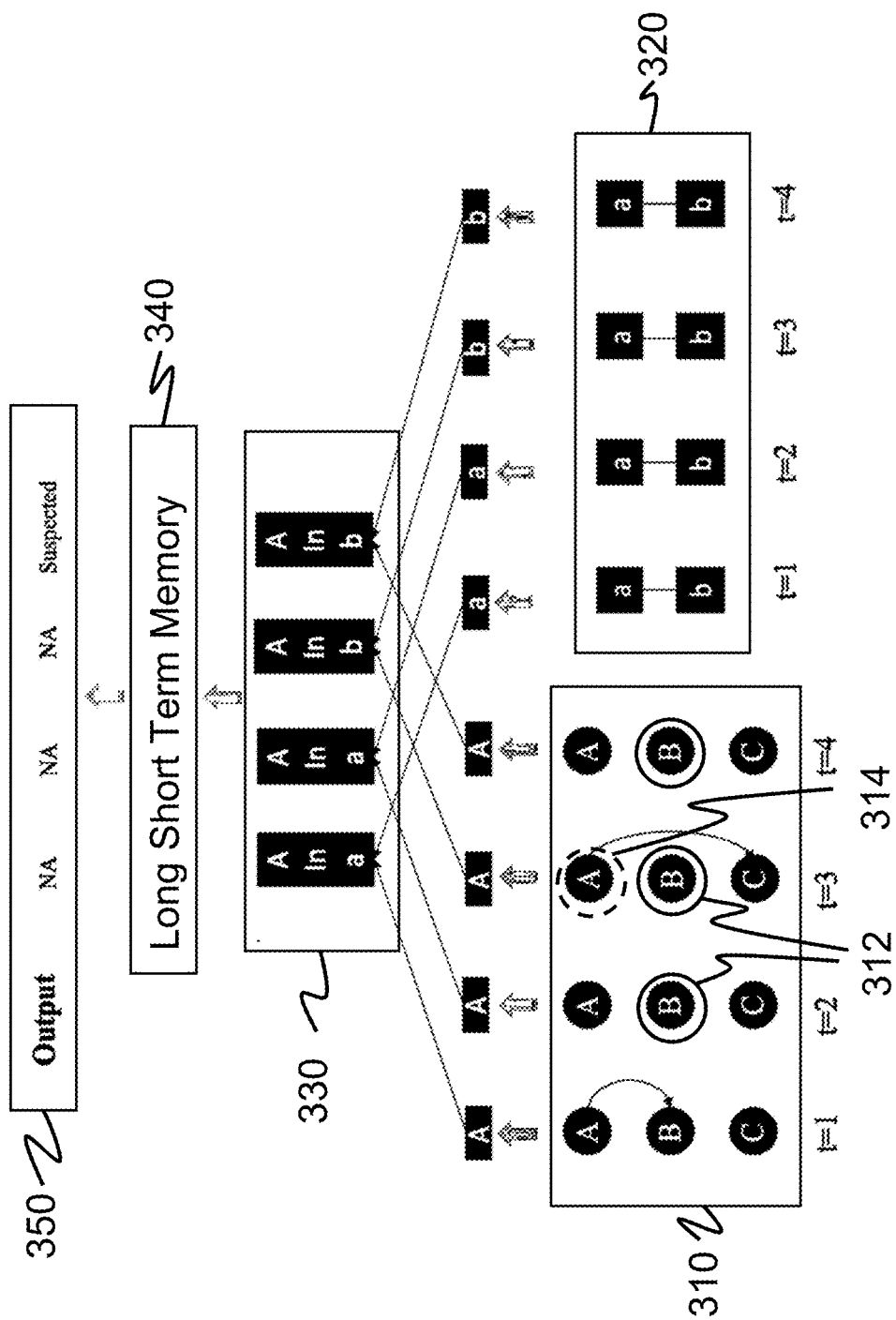
FIG. 3 provides a schematic illustration of a machine learning architecture, according to an embodiment of the invention.

FIG. 3 illustrates a machine learning architecture, according to an embodiment of the invention. As provided in the figure, the method utilizes individual personal and social network data to generate a series of temporal graphs 310, at times $t_1$-$t_4$, for individuals A, B, and C. The temporal graphs indicate interactions between A and B at time t1, as well as interactions between A and C at time $t_3$. Halos 312 indicate a status of 'infected' for individual B at times $t_2$, $t_3$, and $t_4$. Halo 314 indicates self-reported symptoms (fever) of A at time $t_3$.

The method further utilizes city-based data to generate temporal graphs 320 for cities a and b, also at time $t_1$ to $t_4$. The respective time slices $t_1$ to $t_4$, need not be simultaneous slices for the overall method to provide useful infection predictions. Node embeddings for individual A from each of the social network graphs 310, and the city network graphs 320, are combined at block 330, illustrating the movement in this example of individual A from city a to city b at time $t_3$. The combined node embeddings from block 330 are provided as input to a trained LSTM model at block 340. The trained LSTM model 340 evaluates the combined node embeddings and outputs an infection prediction for A based upon input data indicating the movement of A from a to b, as well as A's interactions with B, and C. At 350, the output of the LSTM model indicates a change of A's status from healthy (NA) to 'suspected infection' due to the combination of social interaction and travel plans.

Considering the expansive and changing data sets and need for timely prediction data, large scale computing environments, in an embodiment, the method utilizes computing resources such as cloud and edge cloud systems to provide timely outputs relating to disease progression.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
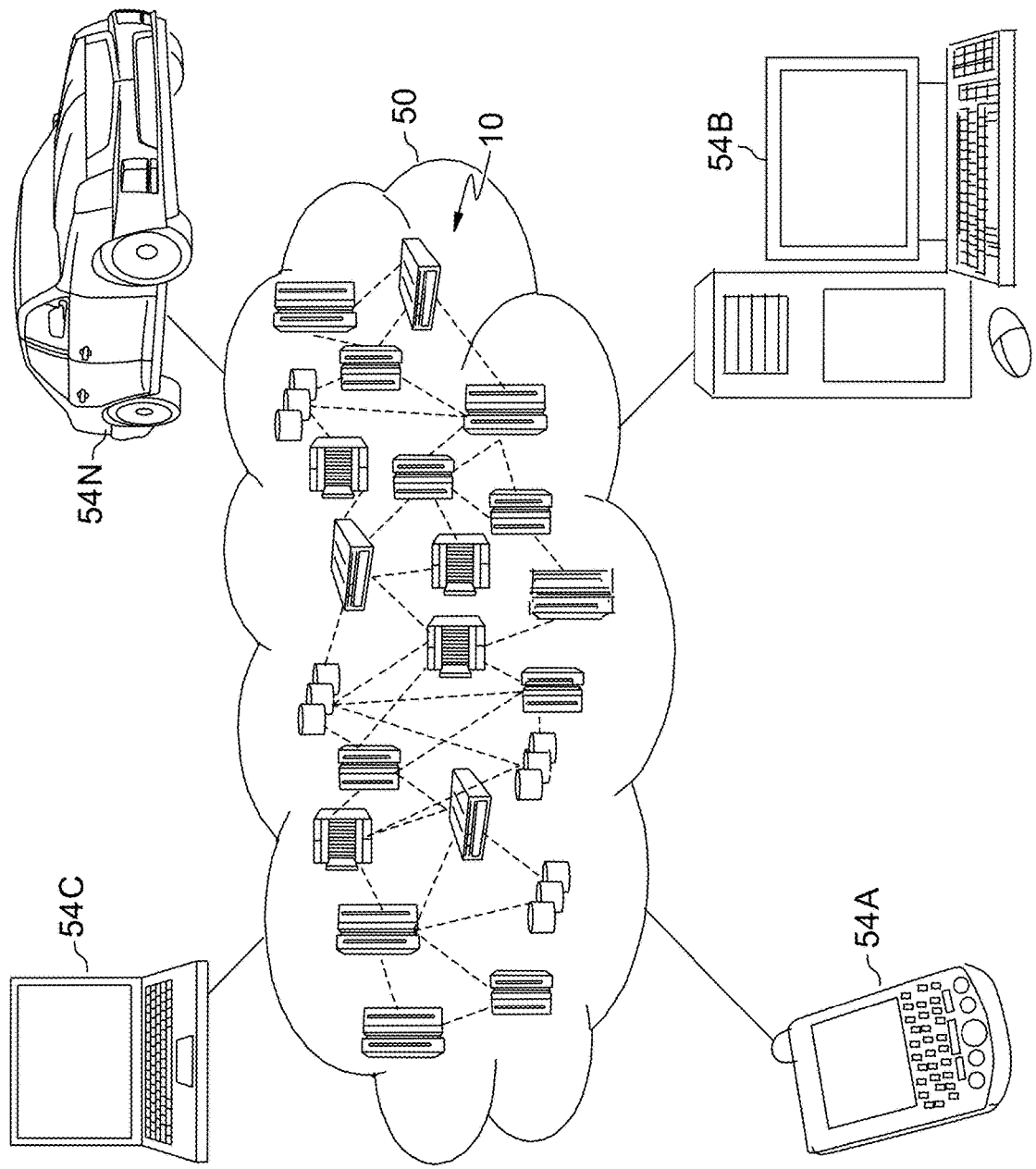
FIG. 4 depicts a cloud computing environment, according to an embodiment of the invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
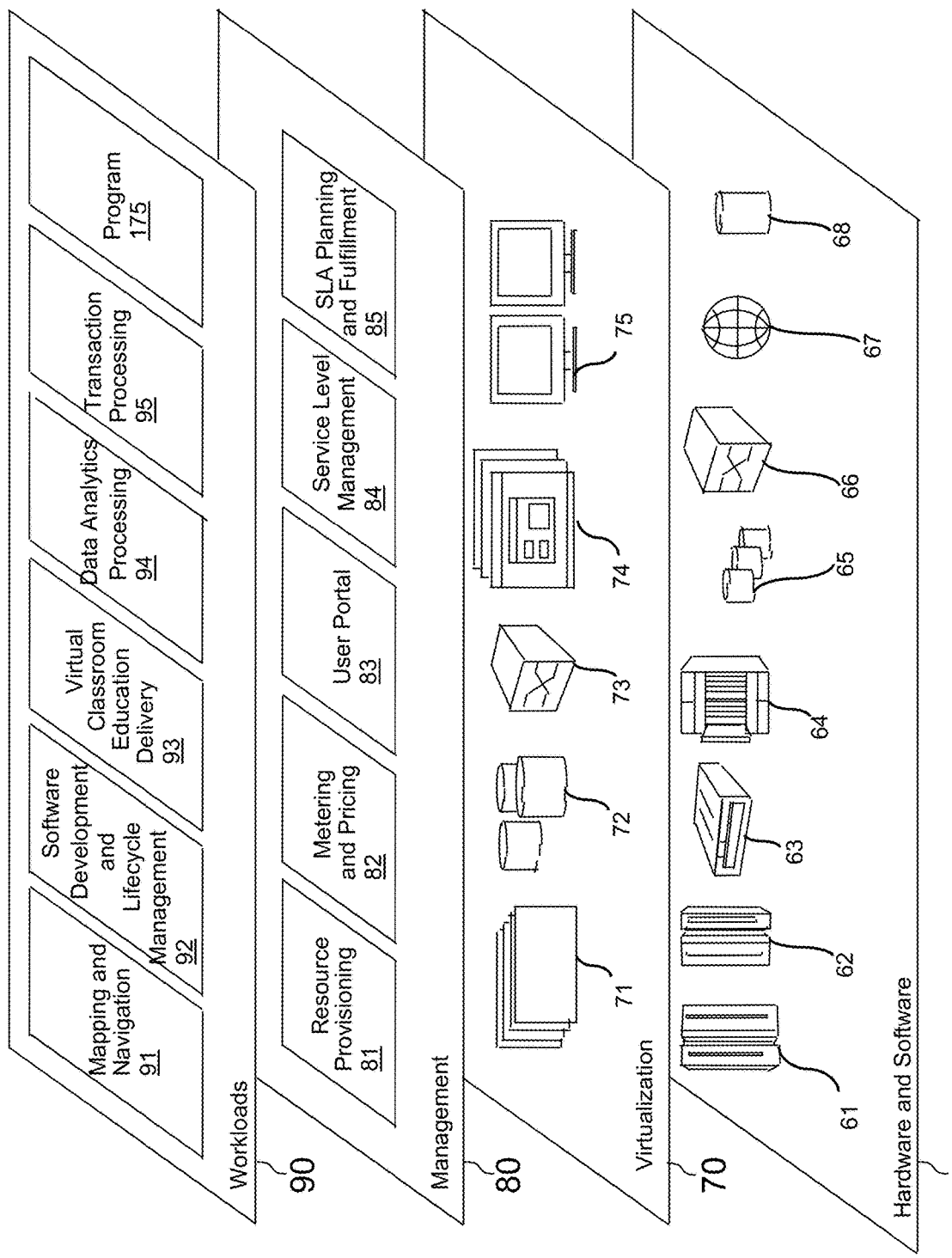
FIG. 5 depicts abstraction model layers, according to an embodiment of the invention.

Referring now to FIG. 5, a set of functional abstraction layers provided by cloud computing environment 50 (FIG. 4) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and infection prediction program 175.

The present invention may be a system, a method, and/or a computer program product at any possible technical detail level of integration. The invention may be beneficially practiced in any system, single or parallel, which processes an instruction stream. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, or computer readable storage device, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer implemented method for predicting infection risk, the method comprising:
    generating, by one or more computer processors, a first temporal graph of a first set of disease progression data;
    generating, by the one or more computer processors, a second temporal graph of a second set of disease progression data;
    combining, by the one or more computer processors, a first temporal graph node embedding and a second temporal graph node embedding;
    generating, by the one or more computer processors, a predicted infection risk according to the combined first temporal graph node embedding and the second temporal graph node embedding;
    generating, by the one or more computer processors, a mapping of safe and hot zones according to the predicted infection risk;
    generating, by the one or more computer processors, a routing from a first safe location to a second safe location according to the mapping and a current location of a user;
    displaying, by the one or more computer processors, the routing as an output on a user device; and
    altering, by the one or more computer processors, the output displayed on the user device to include an alert according to the predicted infection risk and a user location as the user moves along the routing.

2. The computer implemented method according to claim 1, wherein the first set of disease progression data relates to disease progression among a group of individuals.

3. The computer implemented method according to claim 1 wherein the second set of disease progression data relates to disease progression within a geographic area.

4. The computer implemented method according to claim 3, wherein the second set of disease progression data comprises health care system data of the geographic area.

5. The computer implemented method according to claim 4, further comprising generating, by the one or more computer processors, a prediction of a health care system disease response.

6. The computer implemented method according to claim 1, further comprising generating, by the one or more computer processors, a predicted infection risk for a geographic area.

7. The computer implemented method according to claim 1, further comprising generating, by the one or more computer processors, a predicted infection risk for at least one of an individual and a group of individuals.

8. The computer implemented method according to claim 1, further comprising generating, by the one or more computer processors, an alert according to the predicted infection risk.

9. The computer implemented method according to claim 1, further comprising:
    generating, by the one or more computer processors, a predicted infection risk for each of a plurality of geographic locations; and
    generating, by the one or more computer processors, a predicted infection risk for an individual travelling from a first geographic location to a second geographic location according to the predicted infection risks of the geographic locations.

10. The computer implemented method according to claim 1, further comprising:
    generating, by the one or more computer processors, a predicted infection risk for each of a plurality of geographic locations;
    generating, by the one or more computer processors, a mapping of geographic areas according to the predicted infection risks for each of the plurality of geographic locations.

11. A computer program product for predicting infection risk, the computer program product comprising one or more computer readable storage devices and program instructions collectively stored on the one or more computer readable storage devices, the stored program instructions comprising:
    program instructions to generate a first temporal graph of a first set of disease progression data;
    program instructions to generate a second temporal graph of a second set of disease progression data;
    program instructions to combine a first temporal graph node embedding and a second temporal graph node embedding;
    program instructions to generate a predicted infection risk according to the combined first temporal graph node embedding and the second temporal graph node embedding;
    program instructions to generate a mapping of safe and hot zones according to the predicted infection risk;
    program instructions to generate a routing from a first safe location to a second safe location according to the mapping and a current location of a user;
    program instructions to display the routing as an output on a user device; and
    program instructions to alter the output displayed on the user device to include an alert according to the predicted infection risk and a user location as the user moves along the routing.

12. The computer program product according to claim 11, wherein the first set of disease progression data relates to disease progression among a group of individuals.

13. The computer program product according to claim 11, wherein the second set of disease progression data relates to disease progression within a geographic area.

14. The computer program product according to claim 11, the stored program instructions further comprising program instructions to generate a predicted infection risk for a geographic area.

15. The computer program product according to claim 11, the stored program instructions further comprising program instructions to generate a predicted infection risk for an individual.

16. A computer system for predicting infection risk, the computer system comprising:
one or more computer processors;
one or more computer readable storage devices; and
stored program instructions on the one or more computer readable storage devices for execution by the one or more computer processors, the stored program instructions comprising:
program instructions to generate a first temporal graph of a first set of disease progression data;
program instructions to generate a second temporal graph of a second set of disease progression data;
program instructions to combine a first temporal graph node embedding and a second temporal graph node embedding;
program instructions to generate a predicted infection risk according to the combined first temporal graph node embedding and the second temporal graph node embedding;
program instructions to generate a mapping of safe and hot zones according to the predicted infection risk;
program instructions to generate a routing from a first safe location to a second safe location according to the mapping and a current location of a user;
program instructions to display the routing as an output on a user device; and
program instructions to alter the output displayed on the user device to include an alert according to the predicted infection risk and a user location as the user moves along the route.

17. The computer system according to claim 16, wherein the first set of disease progression data relates to disease progression among a group of individuals.

18. The computer system according to claim 16, wherein the second set of disease progression data relates to disease progression within a geographic area.

19. The computer system according to claim 16, the stored program instructions further comprising program instructions to generate a predicted infection risk for a geographic area.

20. The computer system according to claim 16, the stored program instructions further comprising program instructions to generate a predicted infection risk for at least one of an individual and a group of individuals.

* * * * *